US00PP11882P2

(12) United States Plant Patent
Zary

(10) Patent No.: US PP11,882 P2
(45) Date of Patent: May 22, 2001

(54) FLORIBUNDA ROSE PLANT NAMED 'JACYIMP'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/266,994

(22) Filed: Mar. 12, 1999

(51) Int. Cl.[7] ..... A01H 5/00
(52) U.S. Cl. ..... Plt./146
(58) Field of Search ..... Plt./146, 135

*Primary Examiner*—Howard J. Locker
(74) *Attorney, Agent, or Firm*—Klarquist Sparkman Campbell Leigh & Whinston, LLP

(57) ABSTRACT

A floribunda rose plant having vigorous, upright, well-branched growth; glossy, dark green healthy foliage; and rapid repeat flowering of large, fragrant flowers.

1 Drawing Sheet

The present invention relates to a new and distinct variety of rose plant of the floribunda class which was originated by me by crossing the variety 'AFOfres', (not patented, Friesensohne×unnamed seedling), with the variety 'HARroony', U.S. Plant Pat. No. 5,582.

The primary objective of this breeding was to produce a new rose variety having glossy, dark green healthy foliage and rapid repeat flowering from the female and the rich fragrance, large flowers and vigor of the male parent. Flower color was expected to be between the yellow of the female parent and the amber of the male parent. The objective was substantially achieved, along with other desirable improvements, as evidenced by the following unique combination of characteristics that are outstanding in the new variety and that distinguish it from its parents, as well as from all other varieties of which I am aware:

1. Glossy, dark green, disease-resistant foliage.
2. Large, fragrant flowers.
3. Vigorous, upright, well-branched growth.
4. Rapid repeat flowering.

'JACyimp' is a garden floribunda. Its large flowers are very fragrant and when open fully do not expose the reproductive parts. Its filled center gives this modern rose a somewhat old-fashioned look.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'AROfres' (Not patented).

*Pollen parent.*—'HARroony' (U.S. Plant Pat. No. 5,582).

Classification:

*Botanical.*—*Rosa hybrida.*

*Commercial.*—Floribunda.

FLOWER

Observations made from specimens grown in a garden environment at Somis, Calif., in March 1997 to November 1998.

Blooming habit: Recurrent.

Bud:

*Size.*—About 1½ inches long when the petals start to unfurl.

*Form.*—The bud form is long, pointed ovoid.

*Color.*—When sepals first divide, bud color is Yellow-Orange Group 22D. When half blown, the upper sides of the petals are Yellow-Orange Group 22D with fading on the petal margins to Yellow-Orange Group 23D; and the lower sides of the petals are Yellow-Orange Group 22D.

*Sepals.*—Color: Green Group 138B with a blush of Red Group 47C when exposed to bright sun. Surface texture: Covered in fine hair. There are three lightly appendaged sepals. There are two unappendaged sepals with hairy edges.

*Receptacle.*—Color: Green Group 137B. Shape: Apple. Size: Medium, about ½×⅜ inch. Surface: Smooth.

*Peduncle.*—Length: Short, averaging about 2 to 2½ inches. Surface: Smooth. Color: Yellow-Green Group 146C with some blush of Greyed-Purple Group 183B when exposed to bright sun. Strength: Stiff, erect.

Bloom:

*Size.*—Large. Average open size is 4 to 4½ inches.

*Borne.*—Singly and several together in clusters of three to five blooms having rounded shape.

*Stems.*—Strength: Strong. Average length is about 14 to 18 inches.

*Form.*—When first open: High centered. Permanence: Retains its form to the end, outer petals curl back.

*Petalage.*—Number of petals under normal conditions: 35 to 40.

*Color.*—The upper sides of the petals are Yellow-Orange Group 22D with some fading on the petal margins to Yellow-Orange Group 23D. The reverse sides of the petals are Yellow-Orange Group 22D. The base of each petal has on the upper and lower surface a small ⅛×⅛ inch Yellow-Orange Group 21C color spot. The major color on the upper side is Yellow-Orange Group 22D.

*Variegations.*—None.

*Discoloration.*—The general tonality at the end of the first day: No change. At the end of the third day: No change. By day four, there is fading on the upper petal margins from Yellow-Orange Group 22D to Yellow-Orange Group 23D. By days five and six, this fading spreads from petal margins to cover most of the petal.

*Fragrance.*—Strong, spice.

Petals:

*Texture.*—Thick.

*Shape.*—Round.

*Form.*—Tips slightly recurved.

*Arrangement.*—Imbricated. Petaloids in the center: None.

*Persistence.*—Petals drop off cleanly before drying.

*Lastingness.*—On the plant: Fair (about six to seven days). As a cut flower: Fair (about eight to nine days).

Reproductive parts:

*Anthers.*—Size: Medium. Quantity: Many. Color: Yellow-Orange Group 23C. Arrangement: Regular around styles.

*Filaments.*—Color: Yellow-Orange Group 23B.

*Pollen.*—Present.

*Styles.*—Color: Red Group 45C.

*Stigmas.*—Color: Orange-White Group 159C.

Plant:

*Form.*—Bush.

*Growth.*—Virogous, upright, branching. At maturity, height is 3½ feet, width is 2½ feet.

Foliage: Number of leaflets on normal mid-stem leaves: Five or seven.

*Size.*—Large (about 6½ inches long×7 inches wide).

*Quantity.*—Abundant.

*Color.*—New foliage: Upper and lower surfaces: Greyed-Orange Group 176B, quickly turning green. Old foliage: Upper surface: Green Group 136A. Lower surface: Green Group 138A.

Leaflets:

*Shape.*—Oval.

*Texture.*—Leathery.

*Edge.*—Serrated.

*Serration.*—Single, small.

*Petiole rachis.*—Color: Lower: Green Group 147C. Upper: Green Group 137B with some Greyed-Purple Group 183A overlain on the green.

*Petiole underside.*—Smooth, with occasional prickles.

*Stipules.*—Medium (about ¾ inch, bearded and very narrow).

*Disease resistance.*—Mildew and rust resistant, but susceptible to blackspot under normal growing conditions.

Wood:

*New wood.*—Color: Greyed-Orange Group 177A. Bark: Smooth.

*Old wood.*—Color: Green Group 137A. Bark: Smooth.

Prickles:

*Quantity.*—On main canes from base: Ordinary. On laterals from main canes: Ordinary.

*Form.*—Medium, hooked slightly downward.

*Color when young.*—Greyed-Red Group 178A.

*Color when mature.*—Greyed-Orange Group 173D.

Small prickles:

*Quantity.*—On main stalks: None. On laterals: None.

I claim:

1. A new and distinct variety of rose plant of the floribunda class, substantially as herein shown and described, characterized particularly by its vigorous, upright, well-branched growth; glossy, dark green healthy foliage; and rapid repeat flowering of large, fragrant flowers.

* * * * *

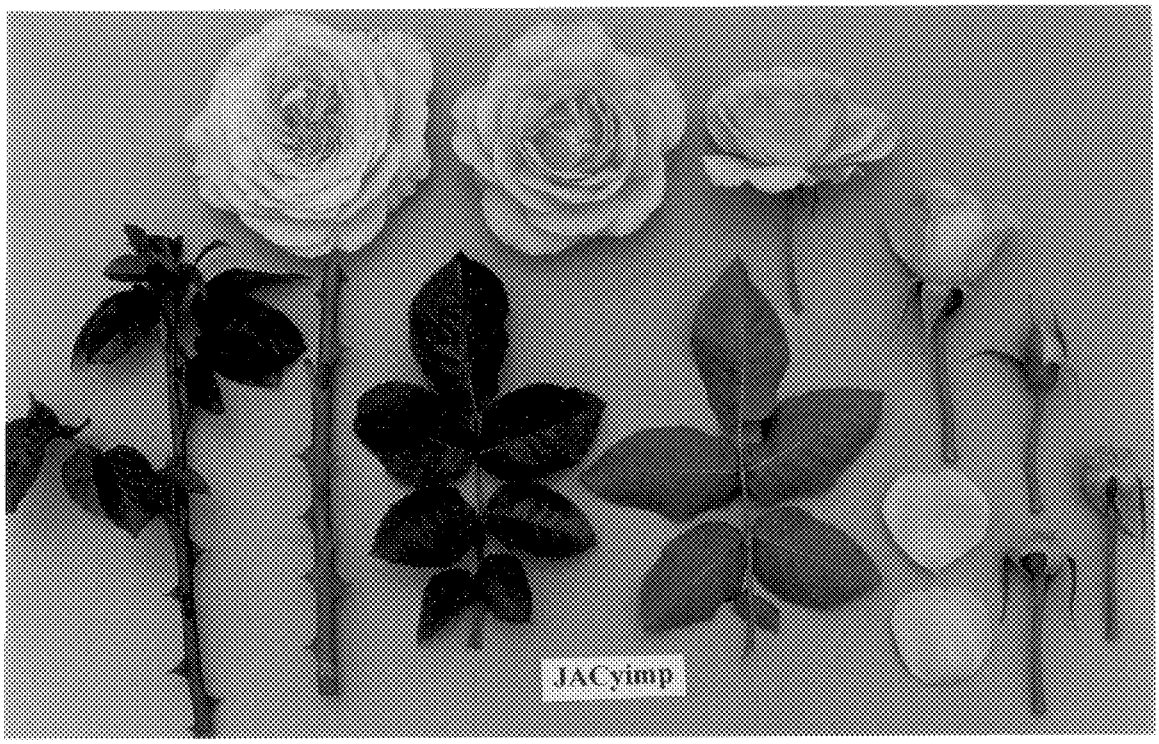
JACyimp